United States Patent
Pan et al.

(10) Patent No.: US 8,304,210 B2
(45) Date of Patent: Nov. 6, 2012

(54) METHOD FOR THE SECRETORY PRODUCTION OF HETEROLOGOUS PROTEIN IN ESCHERICHIA COLI

(75) Inventors: Cheol-Ho Pan, Gangneung-si (KR); Joo Young Lee, Seoul (KR); Byung Hun Um, Seongnam-si (KR); Sang Moo Kim, Yongin-si (KR); Dae-Geun Song, Yongin-si (KR)

(73) Assignee: Korea Institute of Science and Technology, Seoul (KR)

( * ) Notice: Subject to any disclaimer, the term of this patent is extended or adjusted under 35 U.S.C. 154(b) by 150 days.

(21) Appl. No.: 12/919,198

(22) PCT Filed: Feb. 6, 2009

(86) PCT No.: PCT/KR2009/000583
§ 371 (c)(1),
(2), (4) Date: Aug. 24, 2010

(87) PCT Pub. No.: WO2010/085012
PCT Pub. Date: Jul. 29, 2010

(65) Prior Publication Data
US 2011/0033890 A1 Feb. 10, 2011

(30) Foreign Application Priority Data
Jan. 23, 2009 (KR) .................. 10-2009-0006094

(51) Int. Cl.
*C12P 21/06* (2006.01)
(52) U.S. Cl. .................................................... 435/68.1

(58) Field of Classification Search .................. None
See application file for complete search history.

(56) References Cited

U.S. PATENT DOCUMENTS

| | | | |
|---|---|---|---|
| 5,726,044 A | 3/1998 | Lo et al. | |
| 2005/0019857 A1 | 1/2005 | Lee et al. | |

FOREIGN PATENT DOCUMENTS

KR 10-2007-0079025 A 8/2007

OTHER PUBLICATIONS

GenBank Acession No. A8W969, 'RecName: Full=Beta-agarase *AgaB*34; Flags: Precursor' Nov. 25, 2008 See http://www.ncbi.nlm.nih.gov/sviewer/viewer.fcgi?205686180:PROT:7760190.
GenBank Acession No. AAN39119, 'extracellular agarase precursor [*Pseudoalteromonas* sp. CY24]' Apr. 24, 2003 See http://www.ncbi.nim.nih.gov/sviewer/viewer.fcgi?30043922:NCBI:4697495.
International Search Report dated Feb. 17, 2010 for International Application No. PCT/KR2009/000583 (English and Korean).

*Primary Examiner* — Alexander Kim
(74) *Attorney, Agent, or Firm* — Lowe Hauptman Ham & Berner, LLP (57) ABSTRACT

The present invention relates to a signal sequence peptide for the improvement of extracellular secretion efficiency of a heterologous protein in *E. coli*. More particularly, the present invention relates to a gene construct for the improvement of extracellular secretion efficiency of the said heterologous protein in *E. coli*, which comprises a polynucleotide encoding a recombinant protein composed of the heterologous protein linked to C-terminal of the signal sequence peptide represented by SEQ. ID. NO. 3. The present invention contributes to the improvement of extracellular secretion efficiency of a recombinant protein, so that it can be effectively applied to the production of a recombinant protein.

13 Claims, 3 Drawing Sheets

```
  1   M   K   G   F   T   K   H   S   I   L   M   A   C   S   I   G   L   A   I   N    20
  1  ATG AAA GGA TTC ACC AAA CAT TCA ATC TTA ATG GCG TGC AGT ATT GGC TTA GCA ATA AAT    60
 21   A   T   A   A   D   W   D   N   I   P   I   P   A   E   L   D   A   G   Q   S    40
 61  GCA ACA GCT GCT GAT TGG GAT AAC ATC CCC ATT CCT GCC GAA CTA GAC GCA GGA CAA TCT   120
 41   W   E   L   Q   Q   N   Y   S   D   S   F   N   Y   S   G   K   N   S   T   F    60
121  TGG GAG TTA CAA CAA AAC TAT TCT GAC TCT TTT AAC TAC TCA GGC AAA AAC AGC ACG TTT   180
 61   T   G   K   W   K   D   S   Y   F   H   S   W   T   G   P   G   L   T   H   W    80
181  ACC GGC AAA TGG AAA GAC AGT TAC TTT CAT AGC TGG ACA GGC CCA GGC CTT ACT CAC TGG   240
 81   S   S   D   E   S   W   V   G   D   G   N   L   I   I   S   A   S   R   R   Q   100
241  TCG AGC GAT GAA TCG TGG GTT GGT GAC GGC AAC CTC ATC ATT AGT GCT TCG CGT CGC CAG   300
101   G   T   N   K   V   N   A   G   V   I   T   S   K   T   K   V   K   Y   P   I   120
301  GGC ACC AAC AAA GTA AAC GCA GGG GTC ATC ACC TCT AAA ACC AAA GTA AAA TAC CCC ATC   360
121   F   L   E   A   S   I   K   V   S   N   L   E   L   S   S   N   F   W   L   L   140
361  TTT TTA GAA GCC AGT ATC AAG GTG AGT AAC TTA GAG CTT TCA TCC AAC TTC TGG TTG TTA   420
141   S   E   N   D   Q   R   E   I   D   V   L   E   V   Y   G   G   A   R   Q   D   160
421  AGC GAA AAC GAC CAG CGT GAA ATA GAT GTA TTA GAG GTA TAC GGT GGC GCT CGC CAA GAT   480
161   W   Y   A   K   N   M   S   T   N   F   H   V   F   F   R   N   N   D   N   S   180
481  TGG TAC GCT AAG AAC ATG TCG ACC AAC TTT CAT GTT TTC TTC CGT AAT AAC GAC AAC TCG   540
181   I   K   N   D   Y   N   D   Q   T   H   F   T   P   T   W   G   N   Y   W   R   200
541  ATA AAA AAT GAT TAC AAC GAC CAG ACT CAC TTC ACA CCC ACT TGG GGA AAC TAC TGG CGT   600
201   D   G   F   H   R   F   G   V   Y   W   K   S   P   T   D   V   T   F   Y   I   220
601  GAC GGT TTC CAC CGC TTT GGT GTG TAT TGG AAG AGT CCA ACA GAC GTT ACT TTT TAC ATC   660
221   D   G   Q   K   T   T   K   G   A   W   S   Q   V   V   M   K   D   K   D   Y   240
661  GAT GGT CAA AAA ACC ACA AAA GGC GCT TGG AGC CAG GTG GTA ATG AAA GAC AAA GAT TAC   720
241   T   G   A   I   L   D   K   S   R   Y   N   M   D   Q   E   A   F   I   I   I   260
721  ACC GGT GCC ATT CTT GAT AAG AGC CGC TAC AAC ATG GAT CAA GAA GCA TTC ATT ATT ATT   780
261   D   T   E   D   H   S   W   R   S   E   A   G   H   I   A   T   D   A   D   L   280
781  GAT ACT GAA GAC CAC TCT TGG CGC TCT GAA GCA GGC CAC ATC GCC ACT GAT GCA GAT TTA   840
281   A   D   S   D   K   N   K   M   Y   V   D   W   I   R   V   Y   K   P   T   G   300
841  GCC GAC AGT GAT AAA AAC AAG ATG TAT GTA GAT TGG ATC CGC GTT TAC AAA CCA ACG GGC   900
301   G   S   T   T   P   P   T   G   D   I   T   P   P   S   G   Y   T   N   L   Q   320
901  GGT TCC ACT ACC CCA CCT ACT GGC GAT ATT ACG CCA CCG AGT GGT TAC ACC AAT TTA CAA   960
321   L   A   H   S   N   R   C   V   D   V   I   N   G   A   L   W   N   G   S   T   340
961  CTG GCA CAC AGC AAT CGT TGT GTT GAT GTC ATC AAT GGC GCC TTA TGG AAT GGC AGT ACT  1020
341   Y   Q   Q   Y   S   C   N   T   G   N   N   Q   R   F   K   F   T   K   I       360
1021 TAC CAG CAG TAT TCG TGT AAC ACG GGC AAC AAC AAT CAA CGG TTC AAG TTC ACT AAA ATA  1080
361   A   N   N   Q   Y   S   I   N   A   K   V   S   Q   L   C   M   E   L   A   S   380
1081 GCC AAC AAT CAA TAC AGC ATT AAT GCC AAG GTA AGT CAG CTT TGT ATG GAG CTT GCA TCT  1140
381   G   S   S   A   N   G   A   K   V   Q   Q   W   I   C   N   H   A   N   S   N   400
1141 GGC AGC TCG GCA AAT GGC GCT AAG GTG CAG CAA TGG ATA TGT AAT CAC GCC AAC TCT AAT  1200
401   Q   T   W   S   L   E   D   K   G   S   N   T   F   E   I   R   N   K   Q   S   420
1201 CAA ACA TGG AGC CTA GAA GAC AAG GGC AGT AAT ACT TTT GAA ATT AGA AAT AAA CAA AGC  1260
421   G   K   C   L   E   V   A   N   S   S   N   A   N   G   G   Q   I   R   Q   W   440
1261 GGA AAA TGC TTA GAG GTC GCC AAC AGT TCA AAC GCA AAT GGT GGA CAA ATT AGG CAA TGG  1320
441   A   C   T   G   A   T   N   Q   R   F   K   F   L   *                           454
1321 GCC TGC ACT GGC GCG ACT AAC CAG CGC TTC AAA TTC TTG TAG                           1362
```

[FIG. 3]

SEQUENCE LISTING

```
<160> NUMBER OF SEQ ID NOS: 12

<210> SEQ ID NO 1
<211> LENGTH: 1362
<212> TYPE: DNA
<213> ORGANISM: Agarivorans albus strain YKW-34 beta-agarase (agaB34)
      gene

<400> SEQUENCE: 1
atgaaaggat tcaccaaaca ttcaatctta atggcgtgca gtattggctt agcaataaat      60
gcaacagctg ctgattggga taacatcccc attcctgccg aactagacgc aggacaatct     120
tgggagttac aacaaaacta ttctgactct tttaactact caggcaaaaa cagcacgttt     180
accggcaaat ggaaagacag ttactttcat agctggacag gcccaggcct tactcactgg     240
tcgagcgatg aatcgtgggt tggtgacggc aacctcatca ttagtgcttc gcgtcgccag     300
ggcaccaaca aagtaaacgc aggggtcatc acctctaaaa ccaaagtaaa atacccatc     360 tttttagaag ccagtatcaa ggtgagtaac ttagagcttt catccaactt ctggttgtta     420
agcgaaaacg accagcgtga aatagatgta ttagaggtat acggtggcgc tcgccaagat     480
tggtacgcta agaacatgtc gaccaacttt catgttttct tccgtaataa cgacaactcg     540
ataaaaaatg attacaacga ccagactcac ttcacaccca cttggggaaa ctactggcgt     600
gacggtttcc accgctttgg tgtgtattgg aagagtccaa cagacgttac tttttacatc     660
gatggtcaaa aaaccacaaa aggcgcttgg agccaggtgg taatgaaaga caaagattac     720
accggtgcca ttcttgataa gagccgctac aacatggatc aagaagcatt cattattatt     780
gatactgaag accactcttg gcgctctgaa gcaggccaca tcgccactga tgcagattta     840
gccgacagtg ataaaaacaa gatgtatgta gattggatcc gcgtttacaa accaacgggc     900
ggttccacta ccccacctac tggcgatatt acgccaccga gtggttacac caatttacaa     960
ctggcacaca gcaatcgttg tgttgatgtc atcaatggcg ccttatggaa tggcagtact    1020
taccagcagt attcgtgtaa cacgggcaac aacaatcaac ggttcaagtt cactaaaata    1080
gccaacaatc aatacagcat taatgccaag gtaagtcagc tttgtatgga gcttgcatct    1140
```

```
ggcagctcgg caaatggcgc taaggtgcag caatggatat gtaatcacgc caactctaat    1200
caaacatgga gcctagaaga caagggcagt aatactttg  aaattagaaa taaacaaagc    1260
ggaaaatgct tagaggtcgc aacagttca  acgcaaatg  gtggacaaat taggcaatgg    1320
gcctgcactg gcgcgactaa ccagcgcttc aaattcttgt ag                       1362
```

<210> SEQ ID NO 2
<211> LENGTH: 453
<212> TYPE: PRT
<213> ORGANISM: Agarivorans albus strain YKW-34 beta-agarase (agaB34) protein

<400> SEQUENCE: 2

```
Met Lys Gly Phe Thr Lys His Ser Ile Leu Met Ala Cys Ser Ile Gly
1               5                   10                  15

Leu Ala Ile Asn Ala Thr Ala Ala Asp Trp Asp Asn Ile Pro Ile Pro
            20                  25                  30

Ala Glu Leu Asp Ala Gly Gln Ser Trp Glu Leu Gln Gln Asn Tyr Ser
        35                  40                  45

Asp Ser Phe Asn Tyr Ser Gly Lys Asn Ser Thr Phe Thr Gly Lys Trp
50                  55                  60

Lys Asp Ser Tyr Phe His Ser Trp Thr Gly Pro Gly Leu Thr His Trp
65                  70                  75                  80

Ser Ser Asp Glu Ser Trp Val Gly Asp Gly Asn Leu Ile Ile Ser Ala
                85                  90                  95

Ser Arg Arg Gln Gly Thr Asn Lys Val Asn Ala Gly Val Ile Thr Ser
            100                 105                 110

Lys Thr Lys Val Lys Tyr Pro Ile Phe Leu Glu Ala Ser Ile Lys Val
        115                 120                 125

Ser Asn Leu Glu Leu Ser Ser Asn Phe Trp Leu Leu Ser Glu Asn Asp
130                 135                 140

Gln Arg Glu Ile Asp Val Leu Glu Val Tyr Gly Gly Ala Arg Gln Asp
145                 150                 155                 160

Trp Tyr Ala Lys Asn Met Ser Thr Asn Phe His Val Phe Phe Arg Asn
                165                 170                 175

Asn Asp Asn Ser Ile Lys Asn Asp Tyr Asn Asp Gln Thr His Phe Thr
            180                 185                 190

Pro Thr Trp Gly Asn Tyr Trp Arg Asp Gly Phe His Arg Phe Gly Val
        195                 200                 205

Tyr Trp Lys Ser Pro Thr Asp Val Thr Phe Tyr Ile Asp Gly Gln Lys
210                 215                 220

Thr Thr Lys Gly Ala Trp Ser Gln Val Val Met Lys Asp Lys Asp Tyr
225                 230                 235                 240

Thr Gly Ala Ile Leu Asp Lys Ser Arg Tyr Asn Met Asp Gln Glu Ala
                245                 250                 255

Phe Ile Ile Ile Asp Thr Glu Asp His Ser Trp Arg Ser Glu Ala Gly
            260                 265                 270

His Ile Ala Thr Asp Ala Asp Leu Ala Asp Ser Asp Lys Asn Lys Met
        275                 280                 285

Tyr Val Asp Trp Ile Arg Val Tyr Lys Pro Thr Gly Gly Ser Thr Thr
290                 295                 300

Pro Pro Thr Gly Asp Ile Thr Pro Ser Gly Tyr Thr Asn Leu Gln
305                 310                 315                 320

Leu Ala His Ser Asn Arg Cys Val Asp Val Ile Asn Gly Ala Leu Trp
                325                 330                 335
```

Asn Gly Ser Thr Tyr Gln Gln Tyr Ser Cys Asn Thr Gly Asn Asn
            340                 345                 350

Gln Arg Phe Lys Phe Thr Lys Ile Ala Asn Asn Gln Tyr Ser Ile Asn
            355                 360                 365

Ala Lys Val Ser Gln Leu Cys Met Glu Leu Ala Ser Gly Ser Ser Ala
    370                 375                 380

Asn Gly Ala Lys Val Gln Gln Trp Ile Cys Asn His Ala Asn Ser Asn
385                 390                 395                 400

Gln Thr Trp Ser Leu Glu Asp Lys Gly Ser Asn Thr Phe Glu Ile Arg
            405                 410                 415

Asn Lys Gln Ser Gly Lys Cys Leu Glu Val Ala Asn Ser Ser Asn Ala
            420                 425                 430

Asn Gly Gly Gln Ile Arg Gln Trp Ala Cys Thr Gly Ala Thr Asn Gln
            435                 440                 445

Arg Phe Lys Phe Leu
    450

<210> SEQ ID NO 3
<211> LENGTH: 23
<212> TYPE: PRT
<213> ORGANISM: Artificial Sequence
<220> FEATURE:
<223> OTHER INFORMATION: AgaB34 N-terminal 23 ea amino acids

<400> SEQUENCE: 3

Met Lys Gly Phe Thr Lys His Ser Ile Leu Met Ala Cys Ser Ile Gly
1               5                   10                  15

Leu Ala Ile Asn Ala Thr Ala
            20

<210> SEQ ID NO 4
<211> LENGTH: 29
<212> TYPE: DNA
<213> ORGANISM: Artificial Sequence
<220> FEATURE:
<223> OTHER INFORMATION: ASP-Agar_F_Nde I

<400> SEQUENCE: 4
aaacatatga aggattcac caaacattc                                          29

<210> SEQ ID NO 5
<211> LENGTH: 25
<212> TYPE: DNA
<213> ORGANISM: Artificial Sequence
<220> FEATURE:
<223> OTHER INFORMATION: Agar_R_Xho I

<400> SEQUENCE: 5
aaactcgagc aatttgaagc gctgg                                             25

<210> SEQ ID NO 6
<211> LENGTH: 32
<212> TYPE: DNA
<213> ORGANISM: Artificial Sequence
<220> FEATURE:
<223> OTHER INFORMATION: Agar_F_Nde I

<400> SEQUENCE: 6
gaagaacata tggctgattg ggataacatc cc                                     32

<210> SEQ ID NO 7
<211> LENGTH: 21

```
<212> TYPE: DNA
<213> ORGANISM: Artificial Sequence
<220> FEATURE:
<223> OTHER INFORMATION: pET23b_F

<400> SEQUENCE: 7
ggatcgagat ctcgatcccg c                                               21

<210> SEQ ID NO 8
<211> LENGTH: 36
<212> TYPE: DNA
<213> ORGANISM: Artificial Sequence
<220> FEATURE:
<223> OTHER INFORMATION: ASP-R_Nco I_EcoR I

<400> SEQUENCE: 8
aaagaattcc atggcagcag ctgttgcatt tattgc                               36

<210> SEQ ID NO 9
<211> LENGTH: 26
<212> TYPE: DNA
<213> ORGANISM: Artificial Sequence
<220> FEATURE:
<223> OTHER INFORMATION: ASP-GFP_F_Nco I

<400> SEQUENCE: 9
gaagaaccat ggtgagcaag ggcgag                                          26

<210> SEQ ID NO 10
<211> LENGTH: 24
<212> TYPE: DNA
<213> ORGANISM: Artificial Sequence
<220> FEATURE:
<223> OTHER INFORMATION: GFP_F_Nde I

<400> SEQUENCE: 10
gaacatatgg tgagcaaggg cgag                                            24

<210> SEQ ID NO 11
<211> LENGTH: 25
<212> TYPE: DNA
<213> ORGANISM: Artificial Sequence
<220> FEATURE:
<223> OTHER INFORMATION: GFP_R_Xho I

<400> SEQUENCE: 11
gaagaactcg agatctgagt ccgga                                           25

<210> SEQ ID NO 12
<211> LENGTH: 69
<212> TYPE: DNA
<213> ORGANISM: Artificial Sequence
<220> FEATURE:
<223> OTHER INFORMATION: Signal peptide encoding polynucleotide

<400> SEQUENCE: 12
atgaaaggat tcaccaaaca ttcaatctta atggcgtgca gtattggctt agcaataaat     60
gcaacagct                                                             69
```

METHOD FOR THE SECRETORY PRODUCTION OF HETEROLOGOUS PROTEIN IN ESCHERICHIA COLI

CROSS-REFERENCE TO RELATED APPLICATIONS

This application is the U.S. National Stage of International Application No. PCT/KR2009/000583, filed Feb. 6, 2009, which claims the benefit of Korean Patent Application No. 10-2009-0006094, filed Jan. 23, 2009, both of which are hereby incorporated by reference to the extent not inconsistent with the disclosure herewith.

SEQUENCE LISTING

Applicants request that the entry of any sequence listing submission previously filed during the international phase (if originally filed in the PCT International Application and as resubmitted herewith as a *.txt file) be directed into the instant national phase application.

BACKGROUND OF THE INVENTION

1. Field of the Invention

The present invention relates to a signal sequence peptide for the improvement of extracellular secretion efficiency of a heterologous protein in E. coli.

2. Description of the Related Art

As the protein related industry becomes bigger, recombinant proteins are being produced in different expression systems according to the purpose of use and the scale of production. The expression systems are classified by a biological host, and the most representative expression systems are the ones using microorganisms such as E. coli or yeast, insect cells, animal cells, and plant cells, etc. In particular, E. coli expression system is most widely used because it is easy for gene manipulation and economical. However, it has disadvantages for the production of eukaryote-originated proteins such as cytokine because post-translational modification such as glycosylation is not possible in there and protein secretion in a culture medium is difficult. In addition, most proteins are produced as inactive insoluble forms such as inclusion body because of unsatisfactory level of folding of disulfide bond. There have been attempts to overcome these problems by thorough studies of secretion expression, co-expression of molecular chaperon, and re-folding, etc.

The present inventors tried to confirm what elements could improve the efficiency of protein secretion. As a result, the present inventors confirmed that the polypeptide comprising 23 amino acid residues (SEQ. ID. NO. 3) at N-terminal of beta-agarase AgaB34 (Gene Bank Accession NO. EU200967; nts SEQ. ID. NO. 1, aa SEQ. ID. NO. 2) could be used as a signal sequence peptide for the improvement of secretion efficiency of a heterologous protein in E. coli, leading to the completion of the present invention.

SUMMARY OF THE INVENTION

It is an object of the present invention to provide a signal sequence peptide for the improvement of extracellular secretion efficiency of a heterologous protein in E. coli, a polynucleotide encoding the same, and a gene construct containing the same.

It is another object of the present invention to provide an expression vector containing the said gene construct and a transformant transfected with the expression vector.

It is further an object of the present invention to provide a method for improving extracellular secretion efficiency of a heterologous protein in E. coli and a recombinant protein prepared by the said method.

It is also an object of the present invention to provide a method for production of a heterologous protein in its original form.

To achieve the above objects, the present invention provides a signal sequence peptide comprising the polypeptide represented by SEQ. ID. NO. 3 for the improvement of extracellular secretion efficiency of a heterologous protein in E. coli.

The present invention also provides a polynucleotide encoding the said signal sequence peptide.

The present invention further provides a gene construct containing the polynucleotide encoding the recombinant protein composed of the heterologous protein linked to C-terminal of the signal sequence peptide for the improvement of extracellular secretion efficiency of the heterologous protein in E. coli.

The present invention also provides an expression vector containing the said gene construct.

The present invention also provides a transformant transfected with the said expression vector.

The present invention also provides a method for production of a recombinant protein with improved extracellular secretion efficiency in E. coli, comprising the steps of culturing the transformant; inducing the recombinant protein expression; and obtaining the recombinant protein.

The present invention also provides a recombinant protein produced by the said method.

In addition, the present invention provides a method for production of a heterologous protein in its original form.

ADVANTAGEOUS EFFECT

As explained hereinbefore, the present invention can be effectively used to produce a recombinant protein by improving extracellular secretion efficiency of a target recombinant protein.

BRIEF DESCRIPTION OF THE DRAWINGS

The application of the preferred embodiments of the present invention is best understood with reference to the accompanying drawings, wherein:

FIG. 1 is a diagram illustrating the signal sequence and ORF of AgaB34.

DESCRIPTION OF THE PREFERRED EMBODIMENTS

The terms used in this invention are described hereinafter.

In this invention, the term "heterologous protein" or "target protein" indicates a protein that those in the art want to mass-produce. It includes every protein that can be expressed in a transformant transfected with a recombinant expression vector constructed by inserting a polynucleotide encoding the protein.

The term "recombinant protein" or "fusion protein" indicates a protein in which another protein is linked or another amino acid sequence is added to N-terminal or C-terminal of the original heterologous protein. It includes the recombinant fusion protein in which a signal sequence peptide is connected to a target protein or the recombinant protein of a target protein which can be prepared by eliminating a signal sequence from the recombinant fusion protein.

The term "signal sequence peptide" indicates an efficient peptide helping the heterologous protein pass through the intracellular membrane in order to secrete the heterologous protein expressed in virus, prokaryotic cells or eukaryotic cells in periplasm or outer cells.

The term "protease recognition site" indicates the amino acid sequence that a protease recognizes to digest.

The term "expression vector" indicates a linear or a circular DNA molecule comprising a fragment encoding the target polypeptide operably liked to the additional fragment provided for the transcription of a vector. The additional fragment herein includes a promoter sequence and a stop codon sequence. The expression vector includes one or more replication origins, one or more selection markers, one or more tags and polyadenylation signals, etc. The expression vector is generally originated from plasmid or virus DNA or from both of them.

The term "operably linked" indicates that fragments are arranged to be operable during the transcription from promoter to stop codon.

Hereinafter, the present invention is described in detail.

The present invention provides a signal sequence peptide comprising the polypeptide represented by SEQ. ID. NO. 3 for the improvement of extracellular secretion efficiency of a heterologous protein in *E. coli*.

The present invention also provides a polynucleotide encoding the said signal sequence peptide.

The present invention further provides a gene construct containing the polynucleotide encoding the recombinant protein composed of the heterologous protein linked to C-terminal of the signal sequence peptide for the improvement of extracellular secretion efficiency of the heterologous protein in *E. coli*.

The present invention also provides an expression vector containing the said gene construct.

The present invention also provides a transformant transfected with the said expression vector.

The present inventors tried to confirm what elements could improve the efficiency of protein secretion. As a result, in a preferred embodiment of the present invention, the present inventors predicted the possibility of using the polypeptide comprising 23 amino acid residues (SEQ. ID. NO. 3) at N-terminal of beta-agarase AgaB34 (Gene Bank Accession NO. EU200967; nts SEQ. ID. NO. 1, aa SEQ. ID. NO. 2) (see FIG. 1), and further confirmed from the comparison of secretion efficiency between ASP deleted agarase and wild type agarase that extracellular secretion efficiency of ASP deleted agarase was almost zero (see FIG. 2). It was also confirmed that extracellular secretion efficiency of GFP was significantly improved when ASP was fused with the reporter protein GFP (see FIG. 3). Therefore, it was confirmed that ASP could be effectively used for the improvement of extracellular secretion efficiency of the recombinant protein fused with a heterologous protein in *E. coli*.

The polypeptide represented by SEQ. ID. NO. 3 is the signal sequence peptide corresponding to 23 amino acid residues (SEQ. ID. NO. 3) at N-terminal of beta-agarase AgaB34 (Gene Bank Accession NO. EU200967; nts SEQ. ID. NO. 1, aa SEQ. ID. NO. 2), the agarase gene separated from the marine microorganism *Agarivorans albus* YKW-34.

The polynucleotide encoding the said signal sequence peptide is represented by SEQ. ID. NO. 12.

The said heterologous protein herein is not limited, and any protein that is accepted by those in the art can be used. That is, a protein selected from the group consisting of antigen, antibody, cell receptor, enzyme, structural protein, serum, and cellular protein can be expressed as a recombinant protein.

The gene construct herein can additionally include a restriction enzyme site for the insertion of a heterologous gene to be linked to the polynucleotide encoding the signal sequence peptide. The said heterologous gene can be cloned by the restriction enzyme site. The gene construct of the present invention can additionally include the polynucleotide encoding the protease recognition site in between the signal sequence peptide and a heterologous gene. At this time, the added polynucleotide is fused to fit in frame of the gene construct, so that the original form of the heterologous protein can be produced by digesting the secreted protein with the protease. The restriction enzyme recognition site is either one of Xa factor recognition site, enterokinase recognition site, genenase I recognition site, and furin recognition site or two of those linked serially.

In the expression vector above, the polynucleotide encoding the signal sequence peptide and a heterologous protein gene are operably linked on the basic vector. The basic vector is preferably the one selected from the group consisting of pT7, pET/Rb, pGEX, pET28a(+), pET-22b(+) and pGEX, which can transfect *E. coli*. Among them, pET28a(+) is more preferred, but not always limited thereto.

The expression vector is designed to express a recombinant protein once it transfects the host cell, *E. coli*.

The present invention also provides a method for production of a recombinant protein with improved extracellular secretion efficiency in *E. coli*, comprising the steps of culturing the transformant; inducing the recombinant protein expression; and obtaining the recombinant protein.

The present invention also provides a recombinant protein produced by the said method.

The said recombinant protein can be produced by expressing the protein in the transformant transfected with the expression vector of the present invention and recovering thereof. For the recovery, the conventional method well known to those in the art which purifies protein from the cell culture solution can be used.

In addition, the present invention provides a method for production of a heterologous protein in its original form.

Particularly, the present invention provides a method for production of a heterologous protein in its original form comprising the following steps:

1) constructing a recombinant expression vector to which a gene construct comprising a polynucleotide encoding the recombinant protein in which a signal sequence peptide, a protein restriction enzyme recognition site and a heterologous protein are arranged in that order is operably linked;

2) constructing a transformant by transfecting a host cell with the recombinant expression vector of step 1);

3) inducing the expression of the recombinant protein by culturing the transformant of step 2);

4) separating the recombinant protein from the culture solution of step 3); and, 5) separating the original form of the heterologous protein after digesting the recombinant protein prepared in step 4) with a protease that is able to cut the protease recognition site.

The protease recognition site is either one of Xa factor recognition site, enterokinase recognition site, genenase I recognition site, and furin recognition site or two or more of those linked serially.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Construction of Expression Vector

<1-1> Prediction of Signal Sequence Peptide in Agarase

The signal sequence presumed to correspond to 23 amino acid residues (SEQ. ID. NO. 3) at N-terminal of the agarase gene beta-agarase AgaB34 (Gene Bank Accession NO. EU200967; nts SEQ. ID. NO. 1, aa SEQ. ID. NO. 2) separated from the marine microorganism *Agarivorans albus* YKW-34 was named herein as 'agarase signal peptide (ASP)'.

<1-2> Agarase Signal Peptide Deleted Expression Vector

The expression vector pET23b-agarase (WT) to express the said ASP and agarase as a fusion protein and the expression vector pET23b-agarase (ΔASP) to express agarase alone without ASP were constructed. Then, agarose secretion was investigated in *E. coli* in the presence or absence of ASP.

1) Particularly, AgaB34 gene (pUSS1, Fu et al., J. Microbiol. Biotechnol, 2008) was used as a PCR template to construct the vectors pET23b-agarase (WT) and pET23b-agarase (ΔASP). To construct pET23b-agarase (WT), ASP-Agar_F_Nde I (SEQ. ID. NO. 4: 5'-AAA CAT ATG AAA GGA TTC ACC AAA CAT TC-3') and Agar_R_Xho I (SEQ. ID. NO. 5: 5'-AAA CTC GAG CAA TTT GAA GCG CTG G-3') were used as primers. To construct pET23b-agarase (ΔASP), Agar_F_Nde I (SEQ. ID. NO. 6: 5'-GAA GAA CAT ATG GCT GAT TGG GAT AAC ATC CC-3') and Agar_R_Xho I (SEQ. ID. NO. 5) were used as primers. PCR was performed with the reaction mixture (final volume of 50 μl) comprising 1 μl of the template gene, 1 μl of each the forward primer and the reverse primer (10 pmole/μl), 1 μl of 10 mM dNTP, 5 μl of 10×pfu buffer, 0.5 μl of pfu (2.5 U/μl), and 40.5 μl of $H_2O$ as follows: predenaturation at 95° C. for 2 minutes, denaturation at 95° C. for 20 seconds, annealing at 50~60° C. for 40 seconds, polymerization at 72° C. for 3 minutes, and 40 cycles from denaturation to polymerization. The PCR product was transferred to agarose-gel for electrophoresis. The PCR product was electrophoresed on 1.0~1.5% agarose gel, followed by separation and purification by using QIAquick Gel extraction kit (Qiagen, USA). The purified DNA fragment was ligated with pJET1.2/blunt vector (Fermentas, Canada) at 22° C. for 5 minutes, followed by transfection in *E. coli* DH5a. The cells were smeared on LB solid medium containing 50 μg/Ml of ampicillin. The grown colonies were cultured again in LB liquid medium. The gene cloned in pJET1.2/blunt was separated by using DNA-spin™ plasmid DNA Purification kit (iNtRON, Korea). The separated gene was digested with BglII, followed by agarose gel electrophoresis.

2) The PCR product cloned in pJET1.2/blunt was separated by using NdeI and XhoI, which was then ligated to pET23b (+) vector pretreated with the same restriction enzymes to construct the expression vectors pET23b-agarase (WT) and pET23b-agarase (ΔASP). At this time, each expression vector was designed to be expressed as fused with 6 histidines at C-terminal for the convenience of purification of the recombinant protein.

<1-3> Expression Vector in which Signal Sequence Peptide is Fused with GFP

The expression vector pET23b-ASP-GFP that was designed to express ASP/GFP as a fusion protein and the expression vector pET23b-GFP that was designed to express GFP alone without ASP were constructed. Then, GFP secretion was investigated in *E. coli* in the presence or absence of ASP. The expression vector pET23b-ASP that was designed to express pET23b(+) and ASP was constructed as the control vector.

1) Particularly, EGFP gene (Biovision, USA) was used as a PCR template to construct the vectors pET23b-ASP-GFP and pET23b-GFP. To construct pET23b-ASP, pET23b-agarase (WT) was used as a PCR template. For the PCR to construct pET23b-ASP, pET23b_F (SEQ. ID. NO. 7: 5'-GGA TCG AGA TCT CGA TCC CGC-3') and ASP-R_Nco I_EcoR I (SEQ. ID. NO. 8: 5'-AAA GAA TTC CAT GGC AGC AGC TGT TGC ATT TAT TGC-3') were used as primers. For the PCR to construct pET23b-ASP-GFP, ASP-GFP_F_Nco I (SEQ. ID. NO. 9: 5'-GAA GAA CCA TGG TGA GCA AGG GCG AG-3') and GFP_R_Xho I (SEQ. ID. NO. 11: 5'-GAA GAA CTC GAG ATC TGA GTC CGG A-3') were used as primers. For the PCR to construct pET23b-GFP, GFP_F_Nde I (SEQ. ID. NO. 10: 5'-GAA CAT ATG GTG AGC AAG GGC GAG-3') and GFP_R_Xho I (SEQ. ID. NO. 11) were used as primers. The PCR product was cloned in pJET1.2/blunt, which was cloned again in pET23b(+) vector to construct pET23b-ASP, pET23b-ASP-GFP and pET23b-GFP.

<1-4> Protein Expression

Each expression vector constructed in examples <1-2> and <1-3> was transfected in the recombinant protein expressing *E. coli* C41 (DE3). The obtained transformant was inoculated in LB liquid medium supplemented with 50 μl/Ml of ampicillin at the concentration of 0.1%, followed by shaking culture at 37° C. for 14 hours. Cell growth was measured at 600 nm. When $OD_{600}$ reached 0.5, IPTG was added to induce the expression of the recombinant protein at the concentration of 0.5 mM. After adding IPTG, the temperature of the culture was lowered to 30° C., followed by shaking culture for 4 hours. Upon completion of the culture, centrifugation was performed to recover the supernatant and the cells.

<1-5> Extraction of Intracellular Protein

To analyze the recombinant protein in the cytoplasm of *E. coli*, *E. coli* cells were lysed by using a sonicator (Sonic dismembrator model 500, Fisher, USA). Particularly, the *E. coli* cells recovered by centrifugation were suspended in 20 mM Tris-Cl (PH 8.0) buffer. Then, the cells were lysed by sonication at 10% amplitude. This process produced a lot of heat, so that the process was performed with the sample in ice. After lysis, centrifugation was performed at 13,000 rpm, at 4° C. for 5 minutes to remove cell lysate. Agarase enzyme activity in the supernatant was measured.

<1-6> Purification of Extracellular Protein

Centrifugation was performed to remove the *E. coli* cells. The culture solution was equilibrated with buffer A (20 mM Tris-Cl, pH 8.0, 5 mM imidazole, 0.5M NaCl). The equilibrated culture solution was injected in the column filled with His.Bind Resin (Novagen, USA) equilibrated with the same buffer. Non-specific proteins were washed off from the column with buffer B (20 mM Tris-Cl, pH 8.0, 60 mM imidazole, 0.5M NaCl) having the volume of 10 times the volume of the column. The recombinant protein was eluted by using buffer C (20 mM Tris-Cl, pH 8.0, 0.5 M imidazole, 0.5 M NaCl), which was used for the measurement of fluorescence.

Example 2

Measurement of Agarase Activity

Agarase enzyme activity was measured by colorimetry measuring reducing sugar. Particularly, the substrate, 0.1% agarose solution, was put in a 1.5 Ml tube by 400 µl, to which the supernatant obtained from pET23b-agarase (WT) and pET23b-agarase (ΔASP) of example 1 and the intracellular protein sample were added by 100 µl each, followed by inducing enzyme reaction with shaking at 37° C. Upon completion of the enzyme reaction, 500 µl of dinitrosalicylic acid (DNS) solution reacting with reducing sugar was added thereto, followed by boiling at 100° C. for 5 minutes. The tube stayed in ice water for 15 minutes. $OD_{575}$ was measured and the result was compared with the D-galactose standard curve to calculate agarase enzyme activity. 1 unit of agarase enzyme activity was defined by the enzyme amount that could produce 1 µmol of D-galactose.

Figure 2:
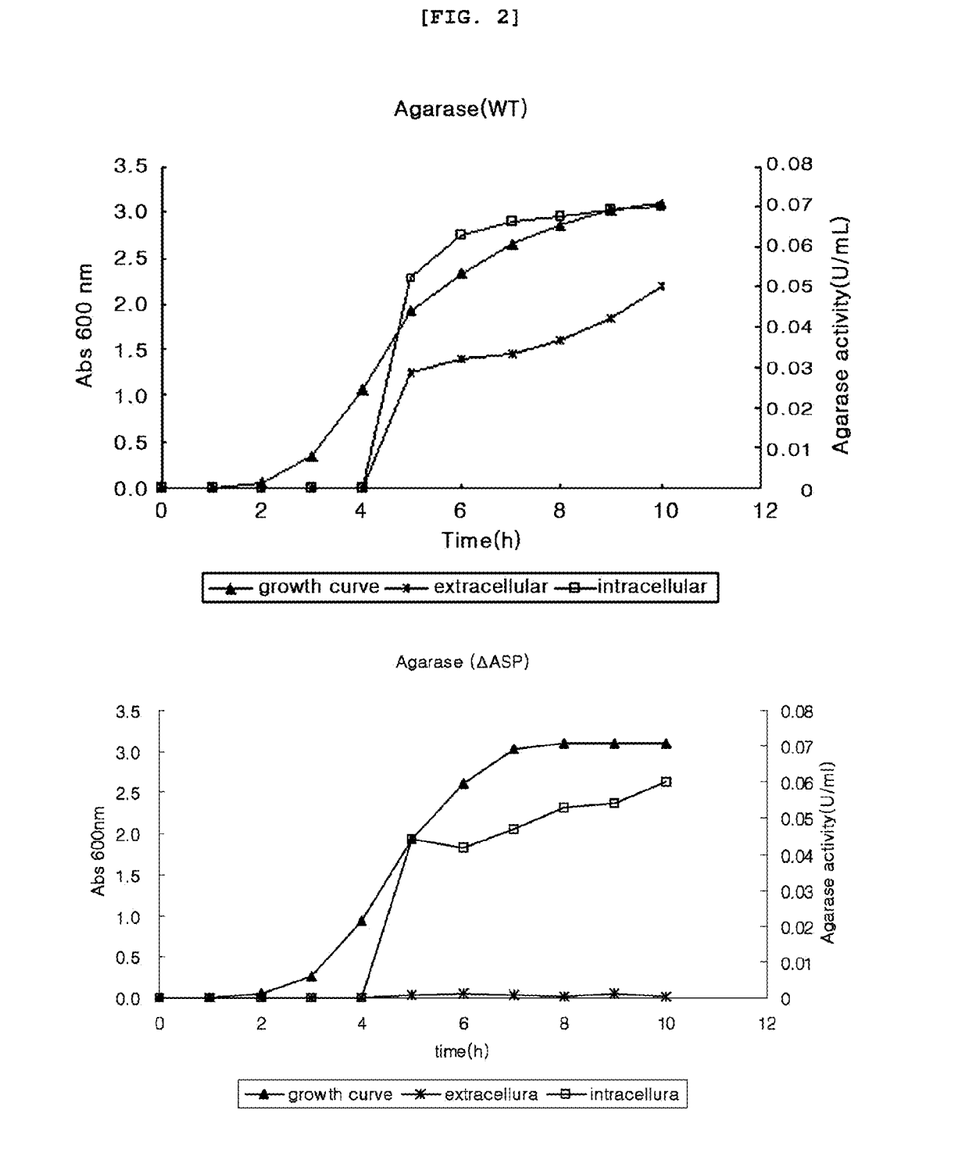
FIG. 2 is a diagram illustrating the inhibition of extracellular secretion of a protein that is agarase in which a signal sequence peptide (ASP) has been deleted:
 2a: ASP has not been deleted; and,
 2b: ASP has been deleted.

As a result, as shown in FIG. 2, the extracellular agarose secretion was high in the presence of ASP, while the extracellular agarase secretion was almost none in the absence of ASP.

Example 3

Measurement of Fluorescence

Figure 3:
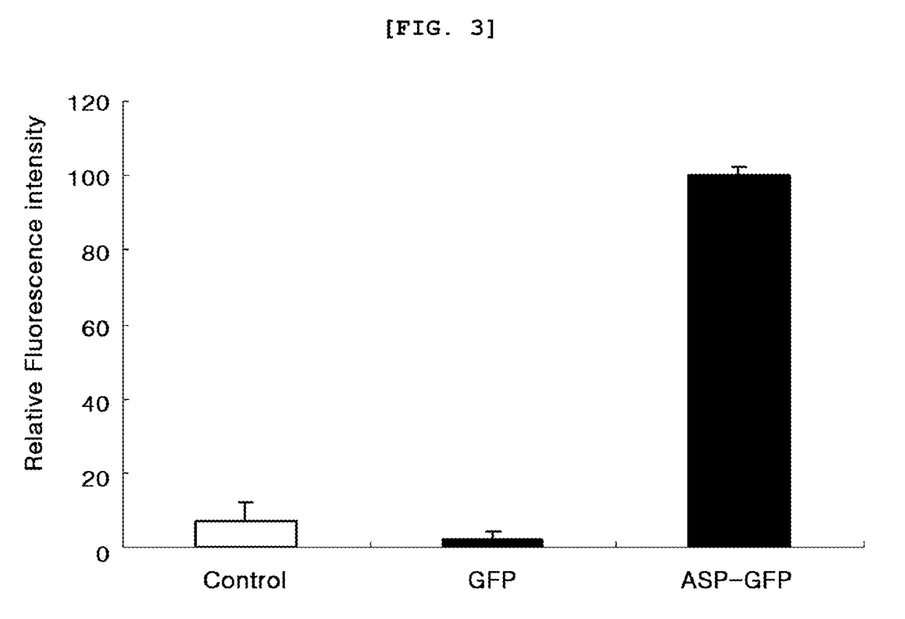
FIG. 3 is a diagram illustrating the improvement of extracellular secretion of the fusion protein of ASP and GFP.

200 µl of each pET23b-ASP, pET23b-ASP-GFP and pET23b-GFP culture solution prepared in example 1 was loaded in a 96-well microplate. Fluorescence of the sample was measured with a multi-microplate reader (Synergy™ HT Multi-Mode Microplate reader, Biotek, USA). At that time, excitation wavelength was 485 nm and emission wavelength was 528 nm. As a result, as shown in FIG. 3, the extracellular secretion of GFP was confirmed to be very high when GFP was fused with ASP.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

---

What is claimed is:

1. A method for producing a recombinant protein with improved extracellular secretion efficiency of a heterologous protein in a host cell, comprising the following steps:
   1) constructing a gene construct comprising a polynucleotide encoding a recombinant protein in which a signal sequence peptide comprising the polypeptide represented by SEQ ID NO: 3, and a heterologous protein fused to C-terminal of the said signal sequence peptide are arranged stepwise;
   2) constructing an expression vector to which the gene construct of step 1) is operably linked;
   3) preparing a transformant by transfecting the host cell with the expression vector of step 2); and 4) obtaining the recombinant protein after inducing the expression of the recombinant protein by culturing the transformant of step 3).

2. The method for producing a recombinant protein according to claim 1, wherein the signal sequence peptide of step 1) is encoded by the polynucleotide represented by SEQ ID NO: 12.

3. The method for producing a recombinant protein according to claim 1, wherein the heterologous protein of step 1) is selected from the group consisting of antigen, antibody, cell receptor, enzyme, structural protein, serum, and cellular protein.

4. The method for producing a recombinant protein according to claim 1, wherein the gene construct of step 1) additionally includes a restriction enzyme site for the insertion of a heterologous gene linked to the polynucleotide encoding the signal sequence peptide.

5. The method for producing a recombinant protein according to claim 1, wherein the gene construct of step 1) additionally includes a polynucleotide encoding a protease recognition site in between the signal sequence peptide and the heterologous gene.

6. The method for producing a recombinant protein according to claim 5, wherein the protease recognition site is either one of Xa factor recognition site, enterokinase recognition site, genenase I recognition site and furin recognition site or two or more of those linked stepwise.

7. The method for producing a recombinant protein according to claim 1, wherein the expression vector of step 2) is selected from the group consisting of pT7, pET/Rb, pGEX, pET28a(+), pET23b(+), pET22b(+) and pGEX.

8. The method for producing a recombinant protein according to claim 1, wherein the host cell of step 3) is *E. coli*.

9. A method for producing a heterologous protein in its original form comprising the following steps:

1) constructing a recombinant expression vector to which a gene construct comprising a polynucleotide encoding a recombinant protein in which a signal sequence peptide comprising the polypeptide represented by SEQ ID NO: 3, a protease recognition site, and a heterologous protein, arranged in that order, is operably linked;
2) constructing a transformant by transfecting a host cell with the recombinant expression vector of step 1);
3) inducing the expression of the recombinant protein by culturing the transformant of step 2);
4) separating the recombinant protein from the culture solution of step 3); and,
5) separating the original form of the heterologous protein after digesting the recombinant protein prepared in step 4) with a protease that is able to cut the protease recognition site.

10. The method for producing a heterologous protein in its original form according to claim 9, wherein the heterologous protein of step 1) is selected from the group consisting of antigen, antibody, cell receptor, enzyme, structural protein, serum, and cellular protein.

11. The method for producing a heterologous protein in its original form according to claim 9, wherein the protease recognition site of step 1) is either one of Xa factor recognition site, enterokinase recognition site, genenase I recognition site and furin recognition site or two or more of those linked stepwise.

12. The method for producing a heterologous protein in its original form according to claim 9, wherein the expression vector of step 1) is selected from the group consisting of pT7, pET/Rb, pGEX, pET28a(+), pET23b(+), pET22b(+) and pGEX.

13. The method for producing a heterologous protein in its original form according to claim 9, wherein the host cell of step 2) is *E. coli*.

* * * * *